(12) United States Patent
Shen et al.

(10) Patent No.: US 12,358,913 B2
(45) Date of Patent: *Jul. 15, 2025

(54) CRYSTAL OF DIARYLTHIOHYDANTOIN COMPOUND

(71) Applicant: CHIA TAI TIANQING PHARMACEUTICAL GROUP CO., LTD., Jiangsu (CN)

(72) Inventors: Chunli Shen, Shanghai (CN); Shenglin Chen, Shanghai (CN); Ting Wang, Shanghai (CN); Fei Liu, Jiangsu (CN); Xin Tian, Jiangsu (CN); Yuing Guo, Shanghai (CN); Lin Zhang, Shanghai (CN); Jiahu Wu, Shanghai (CN)

(73) Assignee: CHIA TAI TIANQING PHARMACEUTICAL GROUP CO., LTD., Jiangsu (CN)

( * ) Notice: Subject to any disclaimer, the term of this patent is extended or adjusted under 35 U.S.C. 154(b) by 933 days.

This patent is subject to a terminal disclaimer.

(21) Appl. No.: 17/427,496

(22) PCT Filed: Jan. 22, 2020

(86) PCT No.: PCT/CN2020/073821
§ 371 (c)(1),
(2) Date: Jul. 30, 2021

(87) PCT Pub. No.: WO2020/156448
PCT Pub. Date: Aug. 6, 2020

(65) Prior Publication Data
US 2022/0009925 A1 Jan. 13, 2022

(30) Foreign Application Priority Data
Feb. 1, 2019 (CN) .......................... 201910104953.5

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01); *C07B 2200/13* (2013.01)

(58) Field of Classification Search
CPC ... C07D 471/04; A61P 35/00; C07B 2200/13; A61K 31/519; A61K 31/4184
USPC ......................................................... 514/259
See application file for complete search history.

(56) References Cited

U.S. PATENT DOCUMENTS

| | | | | |
|---|---|---|---|---|
| 9,611,225 | B2* | 4/2017 | Dwivedi | C07D 233/86 |
| 11,332,465 | B2* | 5/2022 | Shen | C07D 403/10 |
| 2013/0116258 | A1 | 5/2013 | Smith et al. | |
| 2014/0309262 | A1 | 10/2014 | Jung et al. | |
| 2015/0182529 | A1 | 7/2015 | Smith et al. | |
| 2019/0209539 | A1 | 7/2019 | Bignan | |
| 2020/0277290 | A1* | 9/2020 | Shen | C07D 413/10 |
| 2023/0035184 | A1 | 2/2023 | Shen et al. | |

FOREIGN PATENT DOCUMENTS

| | | | |
|---|---|---|---|
| CN | 101817787 | 9/2010 | |
| CN | 102884057 | 1/2013 | |
| CN | 103804358 | 5/2014 | |
| CN | 104105690 | 10/2014 | |
| CN | 104341342 | 2/2015 | |
| CN | 104341352 | 2/2015 | |
| CN | 104341396 | 2/2015 | |
| CN | 106146474 | 11/2016 | |
| EA | 201270720 | 3/2013 | |
| JP | 2019-524711 | 9/2019 | |
| WO | WO 2011/103202 | 8/2011 | |
| WO | WO-2014041487 A2 * | 3/2014 | ............. A61P 35/04 |
| WO | WO 2014/075387 | 5/2014 | |
| WO | WO 2015/018356 | 2/2015 | |
| WO | WO 2017/123542 | 7/2017 | |
| WO | WO 2018/009678 | 1/2018 | |
| WO | WO 2019/037742 | 2/2019 | |
| WO | WO-2019029521 A1 * | 2/2019 | ......... A61K 31/4178 |
| WO | WO 2021/143925 | 7/2021 | |

OTHER PUBLICATIONS

Caira et al. Topics in Current Chemistry, 1998, Design of Organic Solids, Chapter 5, Crystalline Polymorphism of Organic Compounds (Year: 1998).*
Office Action in Chinese Appln. No. 202080011977.7, dated Jun. 17, 2022, 10 pages (with English translation).
International Search Report and Written Opinion in International Appln. No. PCT/CN2020/073821, dated Apr. 22, 2020, 16 pages.
Guo et al., "Design of oxobenzimidazoles and oxindoles as novel androgen receptor antagonists," Bioorganic & Medicinal Chemistry Letters, Apr. 2012, 22(7):2572-2578.
Office Action in Japanese Appln. No. 2020-529797, dated Jul. 19, 2022, 8 pages (with English translation).
Search Report in Chinese Appln. No. CN202110900404 dated Mar. 3, 2022, 2 pages (without English translation).
Greene's Protective Groups in Organic Synthesis, 4th ed., Wuts and Greene (eds)., Apr. 2006, Chapter 2, 351 pages.
International Search Report in International Appln. No. PCT/CN2020/073821, dated Apr. 22, 2020, 3 pages.
Translation of International Search Report for corresponding PCT Appl No. PCT/CN2018/099161, dated Oct. 26, 2018, 3 pages.
Search report in Chinese Appln. No. 202110900404.6 dated Sep. 29, 2022, 6 pages (without English translation).
Design of Organic Solids (Topics in Current Chemistry, 198), 1998 ed., Weber (ed)., 1998, Chapter 5, 46 pages.
Handbook of crystallization of organic compound crystal—Principles and Know-how, Maruzen Publishing Co., Ltd., Jul. 25, 2008, Chapter 4, 22 pages (Abridged Translation).

(Continued)

*Primary Examiner* — Jared Barsky
*Assistant Examiner* — Liyuan Mou
(74) *Attorney, Agent, or Firm* — Fish & Richardson P.C.

(57) ABSTRACT

The present application belongs to the field of medicine, and in particular relates to a crystal of a diarylthiohydantoin compound, a preparation method therefor, and use thereof in the preparation of medicaments for treating related diseases which are androgen-mediated.

9 Claims, 2 Drawing Sheets

(56) References Cited

OTHER PUBLICATIONS

Handbook of Solvents, Kodansha Ltd., 1985, pp. 47-51 (Abridged Translation).
Office Action in Japanese Appln. No. 2021-544623, dated Oct. 30, 2020, 8 pages (Machine Translation).
Office Action in Russian Appln. No. 2021124367/04(051195), mailed Nov. 2, 2023, 18 pages (Machine Translation).
Sherizawa, "Salt and crystal form optimization and crystallization technology," Pharm Tech Japan, 2002, 18(10):81-96 (Abridged Translation).
Technology for the manufacture of solid preparations, CMC Publishing Co., Ltd., 2003, pp. 9, 12-13 (Abridged Translation).
Variankaval et al., "From Form to Function: Crystallization of Active Pharmaceutical Ingredients," AIChE Journal, Jul. 2008, 54(7):1682-1688.
Ivachtchenko et al., "Design, synthesis and biological evaluation of novel 5-oxo-2-thioxoimidazolidine derivatives as potent androgen receptor antagonists," European Journal of Medicinal Chemistry, Jun. 2015, 99:51-66.
Office Action in Israeli Appln. No. 285219, mailed on Mar. 31, 2024, 5 pages.
Polymorphism in Pharmaceutical Solids, 1st ed., Brittain (ed.), Dec. 31, 1999, Table of Contents, 3 pages.

* cited by examiner

CRYSTAL OF DIARYLTHIOHYDANTOIN COMPOUND

The present application is a U.S. National Phase application under 35 U.S.C. § 371 of International Patent Application No. PCT/CN2020/073821, filed on Jan. 22, 2020, which claims the benefit and priority to the Chinese Patent Application No. CN201910104953.5 filed in the China National Intellectual Property Administration on Feb. 1, 2019, the content of each of which is incorporated herein by reference in its entirety.

TECHNICAL FIELD

The present application belongs to the field of medicine, and in particular relates to a crystal of a diarylthiohydantoin compound, a preparation method therefor, and use thereof in the preparation of medicaments for treating related diseases which are androgen-mediated.

BACKGROUND

The androgen receptor (AR) is a steroid receptor in the nuclear receptor superfamily. When bound to androgens (such as testosterone and dihydrotestosterone), AR is released from a complex formed by heat shock proteins for a phosphorylation reaction to form a dimer. The dimer is transferred into a nucleus and bound to a DNA fragment associated therewith, thereby stimulating transcription of its target gene. The transcriptional activity of androgen receptors activated by ligand binding is coordinated by co-activator proteins. AR antagonists have the main function of treating prostatic cancer by directly preventing the binding of testosterone or dihydrotestosterone to androgen receptors and thus blocking the action of androgens on cells, playing the roles of resisting androgens and inhibiting cell growth and finally resulting in apoptosis. Enzalutamide, an androgen receptor antagonist developed by Medivation & Astellas, has been marketed.

In view of the important role of androgen receptor antagonists, it is particularly important to develop androgen receptor antagonists suitable for use as therapeutic drugs.

SUMMARY

The present application provides a crystal of a diarylthiohydantoin compound 2-chloro-4-(3-(2-ethyl-9-fluoro-4-oxo-4H-pyrido[1,2-a]pyrimidin-7-yl)-4,4-dimethyl-5-oxo-2-thioimidazolidin-1-yl)benzonitrile (compound of formula I) for use as an androgen receptor antagonist, which is excellent in terms of at least one of biological activity, safety, pharmacokinetics, bioavailability, hygroscopicity, stability, solubility, purity, easiness in preparation and the like, and thus meets the requirements of production, storage, preparation and the like of medicaments.

In one aspect, the present application provides a crystal of a compound of formula I,

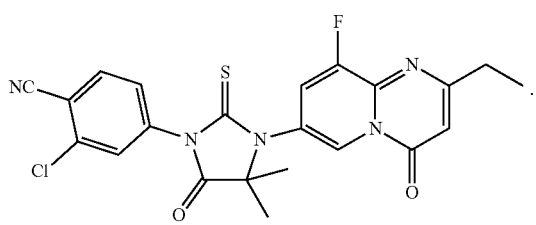

Formula I

In another aspect, the present application provides a crystal of a compound of formula I, wherein, in an X-ray powder diffraction pattern using Cu Kα radiation, diffraction peaks exist at the following 2θ of 13.47°±0.2°, 15.32°±0.2°, 15.98°±0.2°, 18.68°±0.2°, 23.11°±0.2° and 26.41°±0.2°.

In some embodiments of the present application, provided is the crystal of the compound of formula I disclosed herein, wherein in an X-ray powder diffraction pattern using Cu Kα radiation, diffraction peaks exist at the following 2θ of 13.01°±0.2°, 13.47°±0.2°, 14.00°±0.2°, 15.32°±0.2°, 15.98°±0.2°, 18.68°±0.2°, 22.78°±0.2°, 23.11°±0.2°, 24.49°±0.2° and 26.41°±0.2°; in some embodiments of the present application, provided is the crystal of the compound of formula I disclosed herein, wherein in an X-ray powder diffraction pattern using Cu Kα radiation, diffraction peaks exist at the following 2θ of 9.34°±0.2°, 13.01°±0.2°, 13.47°±0.2°, 14.00°±0.2°, 15.32°±0.2°, 15.98°±0.2°, 18.68°±0.2°, 22.78°±0.2°, 23.11°±0.2°, 24.49°±0.2°, 25.85°±0.2°, 26.41°±0.2° and 30.73°±0.2°; in some embodiments of the present application, provided is the crystal of the compound of formula I disclosed herein, wherein in an X-ray powder diffraction pattern using Cu Kα radiation, diffraction peaks exist at the following 2θ of 9.34°±0.2°, 13.01°±0.2°, 13.47°±0.2°, 13.78°±0.2°, 14.00°±0.2°, 15.32°±0.2°, 15.72°±0.2°, 15.98°±0.2°, 18.68°±0.2°, 22.31°±0.2°, 22.78°±0.2°, 23.11°±0.2°, 24.49°±0.2°, 25.85°±0.2°, 26.05°±0.2°, 26.41°±0.2°, 26.65°±0.2° and 30.73°±0.2°; in some embodiments of the present application, provided is the crystal of the compound of formula I disclosed herein, wherein in an X-ray powder diffraction pattern using Cu Kα radiation, diffraction peaks exist at the following 2θ of 9.34°±0.2°, 13.01°±0.2°, 13.47°±0.2°, 13.78°±0.2°, 14.00°±0.2°, 15.32°±0.2°, 15.72°±0.2°, 15.98°±0.2°, 18.68°±0.2°, 19.12°±0.2°, 21.69°±0.2°, 22.31°±0.2°, 22.78°±0.2°, 23.11°±0.2°, 23.39°±0.2°, 24.49°±0.2°, 24.83°±0.2°, 25.38°±0.2°, 25.85°±0.2°, 26.05°±0.2°, 26.41°±0.2°, 26.65°±0.2°, 30.73°±0.2°, 31.08°±0.2°, 32.15°±0.2°, 32.75°±0.2°, 35.50°±0.2° and 35.87°±0.2°.

In some embodiments of the present application, in the X-ray powder diffraction pattern of the crystal of the compound of formula I disclosed herein using Cu Kα radiation, the peak positions and relative intensities of diffraction peaks are shown in Table 1 below:

TABLE 1

Peak positions and relative intensities of diffraction peaks of the X-ray powder diffraction pattern of the crystal of the compound of formula I

| Number | 2θ ± 0.2 (°) | Relative intensity (%) | Number | 2θ ± 0.2 (°) | Relative intensity (%) |
|---|---|---|---|---|---|
| 1 | 9.34 | 9.7 | 15 | 23.39 | 4.5 |
| 2 | 13.01 | 15.8 | 16 | 24.49 | 15.6 |
| 3 | 13.47 | 43.6 | 17 | 24.83 | 4.6 |
| 4 | 13.78 | 7.6 | 18 | 25.38 | 6.4 |
| 5 | 14.00 | 21.3 | 19 | 25.85 | 13.8 |
| 6 | 15.32 | 100.0 | 20 | 26.05 | 14.2 |
| 7 | 15.72 | 9.0 | 21 | 26.41 | 37.0 |
| 8 | 15.98 | 32.0 | 22 | 26.65 | 11.4 |
| 9 | 18.68 | 38.5 | 23 | 30.73 | 14.1 |
| 10 | 19.12 | 7.2 | 24 | 31.08 | 5.7 |
| 11 | 21.69 | 4.9 | 25 | 32.15 | 6.4 |
| 12 | 22.31 | 7.6 | 26 | 32.75 | 4.7 |
| 13 | 22.78 | 19.7 | 27 | 35.50 | 6.7 |
| 14 | 23.11 | 39.3 | 28 | 35.87 | 4.3 |

In some embodiments of the present application, an X-ray powder diffraction (XRPD) pattern of the crystal of the compound of formula I disclosed herein is shown in FIG. 1.

In some embodiments of the present application, the crystal of the compound of formula I disclosed herein has an absorption peak at 238.92° C. according to differential scanning calorimetry (DSC) analysis thereof.

In some embodiments of the present application, a differential scanning calorimetry (DSC) pattern of the crystal of the compound of formula I disclosed herein is shown in FIG. 2.

In some embodiments of the present application, a thermogravimetric analysis (TGA) pattern of the crystal of the compound of formula I disclosed herein is shown in FIG. 3.

In another aspect, the present application provides a preparation method for the crystal of the compound of formula I, comprising mixing the compound of formula I with a solvent to precipitate the crystal.

In some embodiments of the present application, in the preparation method for the crystal of the compound of formula I described above, the mixing time is not less than 48 h.

In some embodiments of the present application, in the preparation method for the crystal of the compound of formula I described above, the mixing is performed under a shaking or stirring condition. In some embodiments of the present application, the mixing is performed under a stirring condition.

In some embodiments of the present application, the preparation method for the crystal of the compound of formula I described above comprises adding the compound of formula I to a solvent to prepare a suspension and then mixing the suspension to precipitate the crystal.

In some embodiments of the present application, in the preparation method for the crystal of the compound of formula I described above, the solvent is selected from the group consisting of methanol, ethanol, ethyl acetate, tetrahydrofuran, acetonitrile, acetone, a combination of methanol and water, a combination of ethanol and water, and a combination of acetone and water.

In some embodiments of the present application, in the preparation method for the crystal of the compound of formula I described above, the solvent is selected from methanol.

In some embodiments of the present application, the volume of the solvent required is 5-50 mL for 1 g of the compound of formula I.

In some embodiments of the present application, the volume of the solvent required is 40 mL for 1 g of the compound of formula I.

In some embodiments of the present application, the preparation method for the crystal of the compound of formula I described above is performed under a heating condition, for example, at a heating temperature of 35-70° C.; in some embodiments of the present application, the heating temperature is 40-60° C.; in some embodiments of the present application, the heating temperature is 40° C.

In some embodiments of the present application, in the preparation method for the crystal of the compound of formula I, the step of mixing is performed in the absence of light.

In some embodiments of the present application, the preparation method for the crystal of the compound of formula I further comprises isolating the precipitated crystal, for example, isolating by filtration or centrifugation; in some specific embodiments of the present application, the method further comprises drying the isolated crystal.

In another aspect, the present application provides a crystalline composition, comprising no less than 50 wt %, preferably no less than 80 wt %, more preferably no less than 90 wt %, most preferably no less than 95 wt % of the crystal of the compound of formula I.

In another aspect, the present application provides a pharmaceutical composition, comprising a therapeutically effective amount of the crystal of the compound of formula I or the crystalline composition thereof. In some embodiments, the pharmaceutical composition disclosed herein further comprises a pharmaceutically acceptable excipient.

In yet another aspect, the present application provides a method for treating androgen-mediated diseases in mammals, comprising administering to a mammal, preferably a human, in need of such treatment a therapeutically effective amount of the crystal of the compound of formula I, or the crystalline composition thereof or the pharmaceutical composition thereof, wherein the diseases include, but are not limited to, a cell proliferative disease (e.g., cancer).

In still another aspect, the present application provides use of the crystal of the compound of formula I or the crystalline composition thereof, or the pharmaceutical composition thereof, in the preparation of medicaments for treating androgen-mediated diseases, wherein the diseases include, but are not limited, a cell proliferative disease (e.g., cancer).

In still yet another aspect, the present application provides use of the crystal of the compound of formula I or the crystalline composition thereof, or the pharmaceutical composition thereof, in the treatment of androgen-mediated diseases, wherein the diseases include, but are not limited, a cell proliferative disease (e.g., cancer).

In still yet another aspect, the present application provides the crystal of the compound of formula I or the crystalline composition thereof, or the pharmaceutical composition thereof, for treating androgen-mediated diseases, wherein the diseases include, but are not limited, a cell proliferative disease (e.g., cancer).

In some embodiments of the present application, the disease is prostate cancer.

In the present application, the instrument for X-ray powder diffraction spectrometry is Bruker D8 Advance ray diffractometer (X-ray tube: Cu, K-Alpha, (u, K-AlpÅ)).

In the present application, the DSC spectrum is determined under the following conditions: instrument: TA Q2000 differential scanning calorimeter; temperature range: 30-300° C.; heating rate: 10° C./min with 50 mL/min N2.

In the present application, TGA thermogravimetric analysis is determined under the following conditions: instrument: TA Q5000IR thermogravimetric analyzer; temperature range: room temperature to 300° C. or loss on drying of 20%; heating rate: 10° C./min with 50 mL/min N2.

For any given crystalline form, the relative intensities of diffraction peaks may vary due to preferred orientations resulting from, e.g., crystal morphology, as is well known in the field of crystallography. The peak intensity varies at a place where there is preferred orientation effect, while it is impossible for the diffraction peak position of crystalline form to vary. In addition, there may be slight errors in the peak positions for any given crystalline form, as is also well known in the field of crystallography. For example, the peak positions may shift due to temperature changes, sample movement or calibration of the instrument when analyzing a sample, and the error in the measurement of 2θ is sometimes about ±0.2 degree, and therefore, it is well known to those skilled in the art that this error should be taken into account when determining each crystalline structure.

The transition temperature is determined by DSC when a crystal absorbs or releases heat due to a change in the crystalline structure or melting of the crystal. For the same crystalline forms of the same compound, the thermal transition temperature and melting point errors in successive analyses are typically within about 5° C., and a given DSC peak or melting point of a compound, when referred to, means the DSC peak or melting point ±5° C. DSC provides an auxiliary method to identify different crystalline forms. Different crystalline morphologies can be identified by their different transition temperatures. It should be noted that, for a mixture, its DSC peak or melting point may vary in a larger range. Furthermore, melting temperature is related to heating rate due to the decomposition of a substance in the melting process.

The "pharmaceutically acceptable excipient" refers to an inert substance administered with active ingredient to facilitate administration of the active ingredient, including, but not limited to, any glidant, sweetener, diluent, preservative, dye/colorant, flavor enhancer, surfactant, wetting agent, dispersant, disintegrant, suspending agent, stabilizer, isotonizing agent, solvent or emulsifier acceptable for use in humans or animals (e.g., domesticated animals) as permitted by the National Medical Products Administration. Non-limiting examples of the excipients include calcium carbonate, calcium phosphate, various sugars and types of starch, cellulose derivatives, gelatin, vegetable oils, and polyethylene glycols.

The term "treating" means administering the compound or formulation described herein to prevent, ameliorate or eliminate a disease or one or more symptoms associated with the disease, and includes:
 (i) preventing the occurrence of the disease or disease state in a mammal, particularly when such a mammal is predisposed to the disease state but has not yet been diagnosed as having it; and
 (ii) inhibiting a disease or disease state, i.e., arresting its development; and
 (iii) alleviating a disease or disease state, i.e., causing its regression.

The term "therapeutically effective amount" refers to an amount of the compound disclosed herein for (i) treating or preventing a specific disease, condition or disorder; (ii) alleviating, relieving or eliminating one or more symptoms of the specific disease, condition or disorder, or (iii) preventing or delaying onset of one or more symptoms of the specific disease, condition or disorder described herein. The amount of the compound disclosed herein composing the "therapeutically effective amount" varies dependently on the compound, the disease state and its severity, the mode of administration, and the age of the mammal to be treated, but can be determined routinely by those skilled in the art in accordance with their knowledge and the present disclosure.

In the following description, certain specific details are included to provide a thorough understanding of various disclosed embodiments. However, those skilled in the relevant art will recognize that the embodiments may be practiced with other methods, components, materials, and the like rather than with one or more of the specific details.

Unless otherwise required, the word "comprise" and variations thereof such as "comprises" and "comprising", used in the specification and claims which follows, should be understood in an open-ended and inclusive sense, i.e., "including, but not limited to".

"One embodiment", "an embodiment", "in another embodiment" or "in some embodiments" used in the specification means that a specific reference element, structure or characteristic described in connection with the embodiment is included in at least one embodiment. Thus, the phrases "in one embodiment", "in an embodiment", "in another embodiment" and "in some embodiments" in various places throughout the specification are not necessarily all referring to the same embodiment. Furthermore, the specific elements, structures, or characteristics may be combined in any suitable manner in one or more embodiments.

It should be understood that, unless otherwise specified clearly, the singular forms "a," "an," and "the" used in the specification and the appended claims include plural referents. Thus, for example, the mentioned reaction including "a catalyst" includes one catalyst, or two or more catalysts. It should be understood that, unless otherwise specified clearly, the term "or" is generally employed in its sense including "and/or".

DETAILED DESCRIPTION

Figure 1:
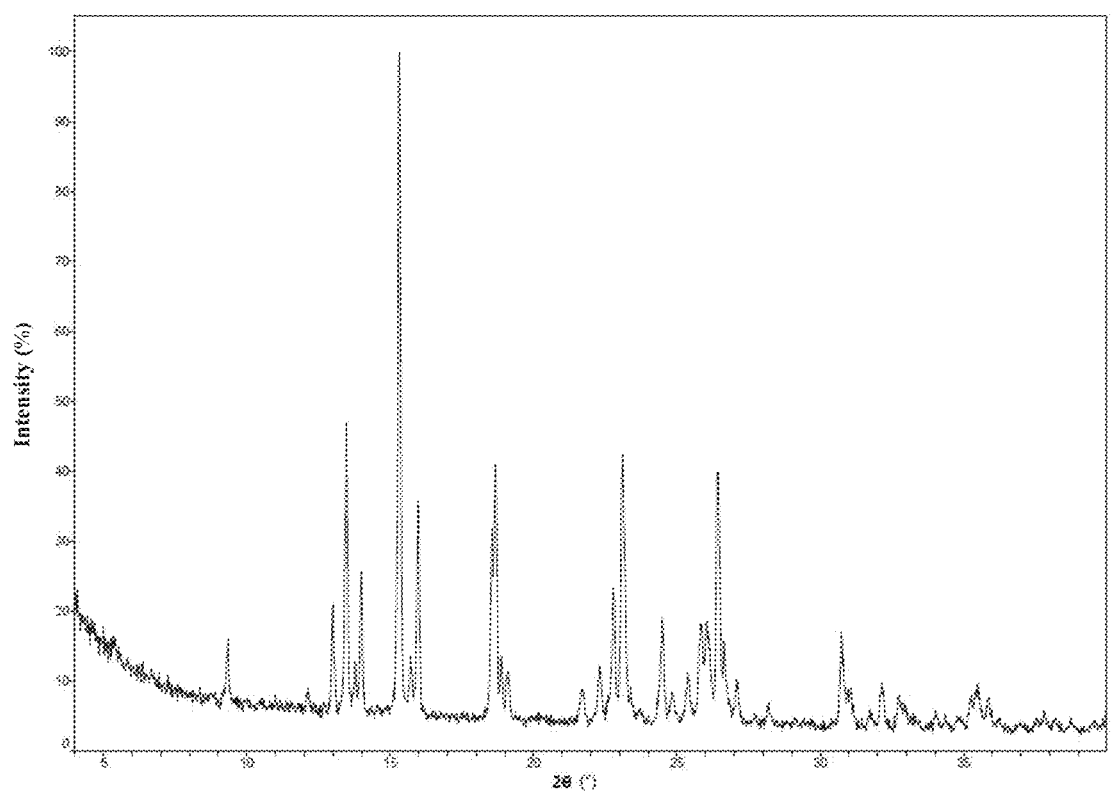
FIG. 1 is an XRPD pattern of a crystal of a compound of formula I prepared in Example 2.

The following specific examples are presented to enable those skilled in the art to more clearly understand and practice the present application. These specific examples should not be considered as limiting the scope of the present application, but merely as being exemplary description and representative of the present application. It should be understood by those skilled in the art that there are other synthesis routes to the compounds of the present application, and the following non-limiting examples are provided.

Unless otherwise stated, all starting materials used in the present application were commercially available and used without further purification. The solvents used in the present application are all commercially available and used without special treatment.

Example 1: Preparation of Compound of Formula I

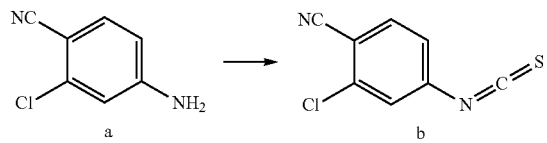 [SMILES: N#Cc1ccc(N)cc1Cl ; N#Cc1ccc(N=C=S)cc1Cl]

Step 1: To a single-neck flask was added water (10 mL), followed by the dropwise addition of thiophosgene (1.13 g). The reaction solution was stirred at 25° C. for 0.5 h under nitrogen atmosphere, then added with Compound a (1.00 g) in portions and stirred at 25° C. for 2 h. The reaction solution was extracted with dichloromethane (10 mL×3), and the organic phase was washed with saturated brine (15 mL), dried over anhydrous sodium sulfate and filtered. The filtrate was concentrated, and the residue was purified by column chromatography to give Compound b. $^1$H NMR (400 MHZ, CDCl$_3$) δ ppm 7.67 (d, J=8.38 Hz, 1H), 7.37 (d, J=1.98 Hz, 1H) 7.21 (dd, J=8.38, 1.98 Hz, 1H).

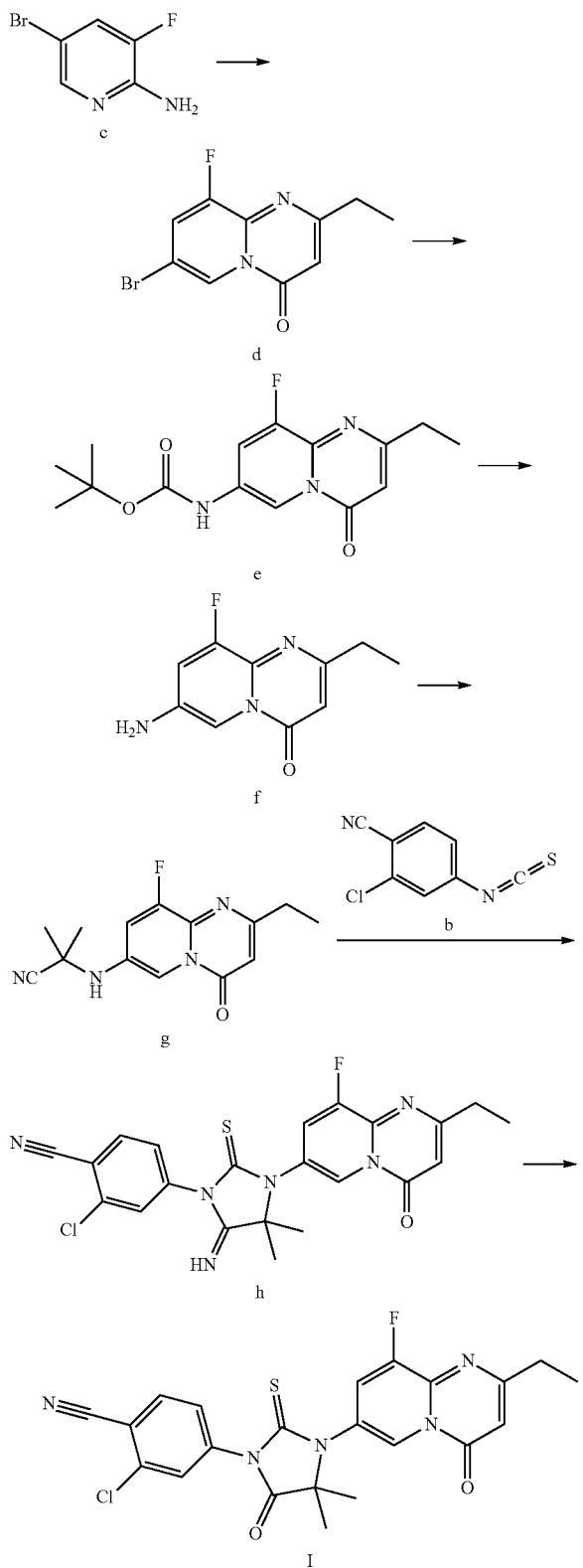

Step 2: To a solution of Compound c (4.00 g) in acetic acid (40 mL) was added methyl propionlyacetae (4.00 g).

The reaction solution was heated to 110° C. and stirred for 94 h. The reaction solution was then supplemented with methyl propionlyacetae (8.26 g), stirred for 16 h, and concentrated. The concentrate was diluted with ethyl acetate (80 mL), and added with a saturated aqueous sodium bicarbonate solution (80 mL). After liquid separation, the organic phase was washed with saturated brine (80 mL), dried over anhydrous sodium sulfate, filtered, and concentrated. The residue was purified by silica gel column chromatography to give Compound d. $^1$H NMR (400 MHZ, CDCl$_3$) δ ppm 8.89 (s, 1H), 7.45 (dd, J=2.0, 8.0 Hz, 1H), 6.36 (s, 1H), 2.70 (q, J=7.5 Hz, 2H), 1.25 (t, J=7.5 Hz, 3H).

Step 3: To a microwave tube were added Compound d (500 mg), tert-butyl carbamate (324 mg), cesium carbonate (1.50 g), 4,5-bis(diphenylphosphino)-9,9-dimethylxanthene (107 mg), bis(dibenzylideneacetone) palladium (170 mg) and toluene (6 mL). The tube was sealed and the reaction solution was reacted under microwave at 120° C. for 30 min. The reaction solution was filtered and washed with ethyl acetate (20 mL), and the filtrate was concentrated under reduced pressure. The residue was purified by silica gel column chromatography to give Compound e. $^1$H NMR (400 MHZ, CDCl$_3$) δ ppm 8.90 (s, 1H), 8.15 (br s, 1H), 7.57 (br s, 1H), 6.32 (s, 1H), 2.71 (q, J=7.5 Hz, 2H), 1.49 (s, 9H), 1.26 (t, J=7.5 Hz, 3H).

Step 4: To a solution of Compound e (200 mg) in dichloromethane (2 mL) was added trifluoroacetic acid (0.4 mL). The resulting reaction solution was stirred at 26° C. for 4 h, added with a saturated aqueous sodium bicarbonate solution (pH of about 7) and extracted with dichloromethane (20 mL). The organic phase was washed with saturated brine (15 mL), dried over anhydrous sodium sulfate, and concentrated under reduced pressure to give Compound f. LCMS (ESI) m/z: 208 (M+1).

Step 5: To a dry reaction flask were added Compound f (300 mg), zinc chloride (59 mg), sodium sulfate (823 mg), acetone (505 mg), trimethylsilyl cyanide (431 mg) and tetrahydrofuran (3 mL). The reaction solution was reacted at 25° C. for 4 h under nitrogen atmosphere. The reaction solution was directly concentrated, and the residue was purified by preparative TLC to give Compound g. $^1$H NMR (400 MHZ, CDCl$_3$) δ ppm 8.52 (s, 1H), 7.33 (dd, J=9.98, 2.32 Hz, 1H), 6.46 (s, 1H), 2.78 (q, J=7.65 Hz, 2H), 1.78 (s, 6H), 1.33 (t, J=7.59 Hz, 3H).

Step 6: To a dry reaction flask were added Compound g (200 mg), Compound b (568 mg), toluene (2 mL) and DMF (0.5 mL). Under nitrogen atmosphere, the reaction solution was added with sodium hydride (44 mg, 60% purity) and reacted at 25° C. for 0.5 h. The reaction solution was concentrated, and the residue was purified by column chromatography to give Compound h.

Step 7: To a dry reaction flask were added Compound h (110 mg), toluene (1.1 mL) and glacial acetic acid (1.1 mL). The reaction solution was reacted at 110° C. for 16 h under nitrogen atmosphere. The reaction solution was concentrated, and the residue was purified by prep-HPLC to give a compound of formula I in amorphous form as determined by X-ray powder diffraction. $^1$H NMR (400 MHZ, CDCl$_3$) δ ppm 8.83 (s, 1H), 7.84 (d, J=8.16 Hz, 1H), 7.68 (d, J=1.98 Hz, 1H), 7.51 (dd, J=8.27, 2.09 Hz, 1H), 7.41 (dd, J=8.71, 2.09 Hz, 1H), 6.49 (s, 1H), 2.82 (q, J=7.57 Hz, 2H), 1.68 (s, 6H), 1.36 (t, J=7.61 Hz, 3H). LCMS (ESI) m/z: 470 (M+1).

Example 2: Preparation of Crystal of Compound of Formula I

Figure 2:
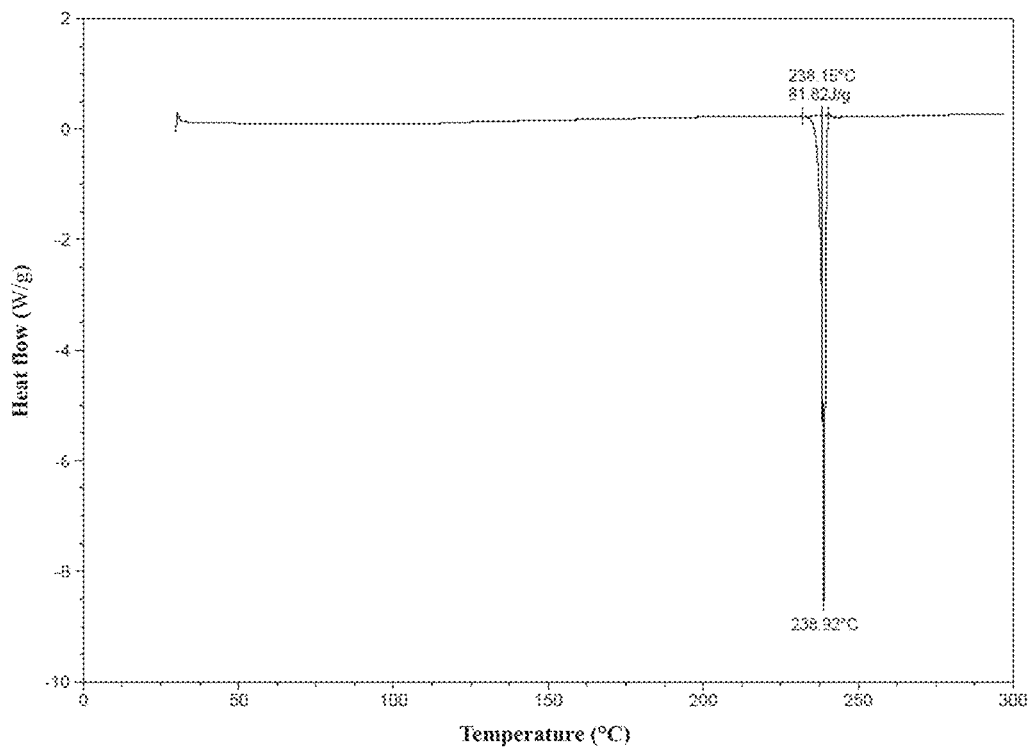
FIG. 2 is a DSC pattern of a crystal of a compound of formula I prepared in Example 2.
Figure 3:
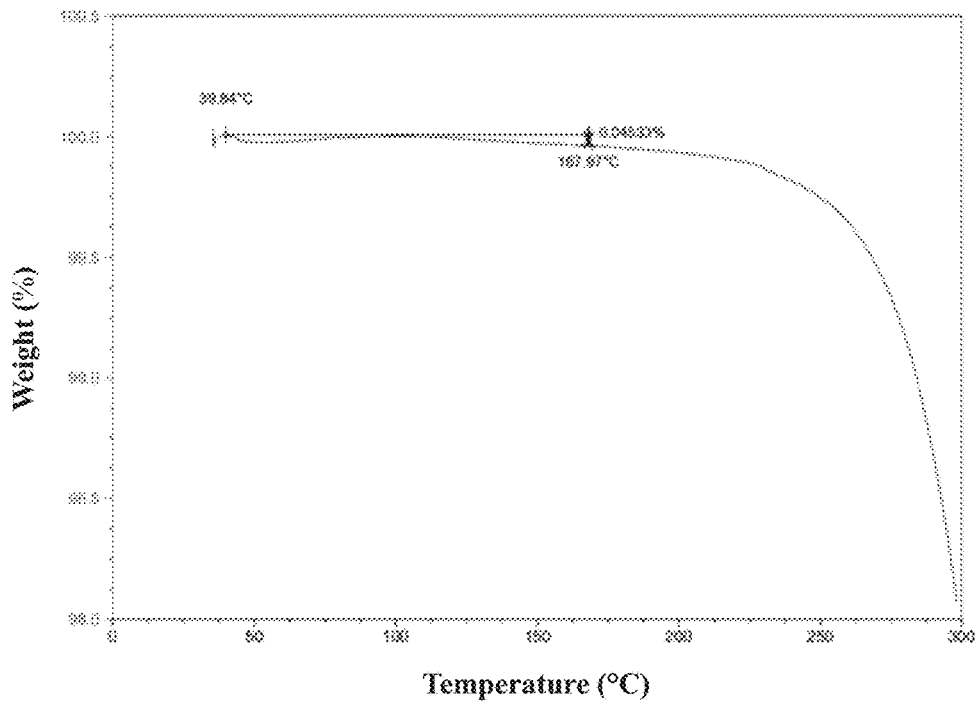
FIG. 3 is a TGA pattern of a crystal of a compound of formula I prepared in Example 2.

To a reaction flask (4.0 mL) were added the compound of formula I (50.1 mg) prepared according to Example 1 and methanol (2.0 mL) to give a suspension. The suspension was placed on a magnetic heating stirrer (40° C.) for stirring (in the absence of light), stirred at 40° C. for 2 days, and centrifuged to separate out a solid. The solid was dried overnight to give a crystal of the compound of formula I. The XRPD results of the resulting crystal are shown in FIG. 1, the DSC results are shown in FIG. 2, and the TGA results are shown in FIG. 3.

Example 3: Antagonism of Androgen Receptor (AR) Nuclear Transport by Compound of Formula I 1. The PathHunter NHR cell line was thawed, cultured and amplified.
2. Cells were seeded onto a 384-well plate before testing and incubated at 37° C. The culture serum had been filtered with charcoal-dextran to reduce the hormone level therein.
3. In antagonistic function detection, the compound was added to the cells and incubated for 60 min, and the working concentrations of the compound of formula I, obtained by dilution from 10 μM in a 3-fold concentration gradient, were 10000 nM, 3333.3 nM, 1111.1 nM, 370.4 nM, 123.5 nM, 41.2 nM, 13.7 nM and 4.67 nM. Then an agonist 6α-fluoroestosterone at 0.06 μM (the concentration is $EC_{80}$, i.e., compound concentration for 80% agonism). Then the mixture was incubated at 37° C. or room temperature for 3-16 h.
4. Signal detection: 12.5 μL or 15 μL (50%, v/v) Path-Hunter detection mixture (kit: DiscoverX; catalog No.: 93-0001 series) was added and the mixture was incubated at room temperature for 1 h. The chemiluminescence signal was read by a PerkinElmer Envision™ instrument.
5. Data analysis: compound activity was analyzed using CBIS data analysis software (ChemInnovation, CA), and the inhibition percentage of the antagonist was calculated as follows: $IC_{50}$ inhibition rate (%)=100%×(1−(average RLU value of test compound−average RLU value of blank control group)/(average RLU value of $EC_{80}$ control−average RLU value of blank control group)).

The test results of antagonism of androgen receptor (AR) nuclear transport by the compound of formula I of Example 1 show that $IC_{50}$ is 0.95 μM.

Example 4: Pharmacokinetic Test of Compound of Formula I

1. Abstract

Taking male CD-1 mice as test animals, the drug concentrations in the plasma of the mice at different time points after intravenous and intragastric administration of the compound of formula I were determined by an LC/MS/MS method. This example aims to investigate the pharmacokinetic performance of the compound of formula I in mice and to evaluate the pharmacokinetic characteristics.

2. Experimental Scheme 2.1 Test Drug: Compound of Formula I 2.2 Test Animals: 4 Healthy Adult Male CD-1 Mice, which were Divided into 2 Groups (2 Mice in Each Group) According to the Body Weight. Animals were Purchased from Shanghai Sippe-Bk Lab Animal Co., Ltd., and Animal Production License Number was SCXK (Shanghai) 2013-0016.

2.3 Drug Preparation

An appropriate amount of sample was weighed, and sequentially added with an appropriate amount of DMSO, PEG400 and water according to the volume ratio of 10:40:50, and the mixture was stirred and ultrasonicated to a clear state (0.4 mg/mL) for intravenous administration.

An appropriate amount of sample was weighed and added into 0.5% CMC+0.2% Tween 80 solution, and the mixture was stirred and ultrasonicated to a suspension state (0.4 mg/mL) for intragastric administration.

2.4 Administration

Four male CD-1 mice were divided into 2 groups, and after fasting overnight, the mice in the first group were subjected to intravenous administration at a volume of 2.5 mL/kg and a dosage of 1 mg/kg, and the mice in the second group were subjected to intragastric administration at a volume of 5 mL/kg and a dosage of 2 mg/kg.

3. Operations

Male CD-1 mice, after intravenous administration of the compound of formula I, were subjected to 30 μL of blood collection at 0.0833, 0.25, 0.5, 1, 2, 4, 8, 24, and 48 h, and the blood was placed in tubes containing 2 μL of EDTA-K2. Male CD-1 mice, after intragastric administration of the compound of formula I, were subjected to 30 μL of blood collection at 0.25, 0.5, 1, 2, 4, 8, 24, and 48 h, and the blood was placed in tubes containing 2 μL of EDTA-K2. The tubes were centrifuged at 3000 g for 15 min to separate out the plasma, which was stored at −60° C. The animals were allowed to eat 4 h after administration.

LC/MS/MS method was used to determine the content of the test compound in the plasma of mice after intravenous and intragastric administration. The linear range of the method was 2.00-6000 nmol/L; plasma samples were analyzed after treatment with acetonitrile to precipitate proteins.

The results of the pharmacokinetic test of the compound of formula I are shown in Table 2 below.

TABLE 2

Results of pharmacokinetic test of the compound of formula I

| Test compound | Mode of administration | Administration dosage | Blood concentration $C_{max}$ (nM) | Time to peak $T_{max}$ (h) | Half life $T_{1/2}$ (h) | Apparent volume of distribution $V_{dss}$ (L/kg) | Clearance Cl (mL/min/kg) | Curve area (0 − t) $AUC_{0-last}$ (nM.h) | Curve area (0 − inf) $AUC_{0-inf}$ (nM.h) | Bio-availability (%) |
|---|---|---|---|---|---|---|---|---|---|---|
| Compound of formula I of Example 1 | Intravenous administration | 1 mg/kg | — | — | 36.6 | 0.248 | 0.0794 | 271453 | 447238 | — |

TABLE 2-continued

Results of pharmacokinetic test of the compound of formula I

| Test compound | Mode of administration | Administration dosage | Blood concentration $C_{max}$ (nM) | Time to peak $T_{max}$ (h) | Half life $T_{1/2}$ (h) | Apparent volume of distribution $V_{dss}$ (L/kg) | Clearance Cl (mL/min/kg) | Curve area (0 – t) $AUC_{0-last}$ (nM.h) | Curve area (0 – inf) $AUC_{0-inf}$ (nM.h) | Bio-availability (%) |
|---|---|---|---|---|---|---|---|---|---|---|
| | Intragastric administration | 2 mg/kg | 12850 | 8.00 | ND | — | — | 369659 | ND | 68.1 |

Note:
"—" indicates that the item does not need to be tested;
ND indicates that the data is not detected.

Example 5: Tissue Distribution Test of Compound of Formula I

1. Abstract

Taking male CD-1 mice as test animals, the drug concentrations in the plasma and brain of the mice after intragastric administration of the compound of formula I were determined by an LC/MS/MS method.

2. Experimental Scheme 2.1 Test Drug: Compound of Formula I 2.2 Test Animals: 2 Healthy Adult Male CD-1 Mice. Animals were Purchased from Shanghai Sippe-Bk Lab Animal Co., Ltd.

2.3 Drug Preparation

An appropriate amount of sample was added into 0.5% CMC/0.2% Tween aqueous solution, and the mixture was stirred and ultrasonicated to a suspension state (0.4 mg/mL).

2.4 Administration

Two male CD-1 mice, after fasting overnight, were subjected to intragastric administration at a volume of 5 mL/kg and a dosage of 2 mg/kg.

3. Operations

Male CD-1 mice, after intragastric administration of the compound of formula I, were subjected to 100 μL of blood collection by cardiac puncture at 4 h, and the blood was placed in tubes containing 2 μL of EDTA-K2 and centrifuged at 3000 g for 15 min to separate out 30 μL of plasma, which was stored at −60° C. Meanwhile, brain tissues were collected, washed, homogenized with 9-fold 15 mM PBS/MeOH (v: v, 2:1), and stored at −60° C. The animals were allowed to eat 4 h after administration.

LC/MS/MS method was used to determine the content of test compound in the plasma and brain of mice after intragastric administration. The linear range of the method was 2.00-6000 nmol/L; plasma samples were analyzed after treatment with acetonitrile to precipitate proteins.

The results of the tissue distribution test are shown in Table 3.

TABLE 3

Results of tissue distribution test

| Compound | Concentration in plasma (nM) | Concentration in brain (nmol/kg) | Brain-to-blood ratio |
|---|---|---|---|
| Compound of formula I of Example 1 | 8260 | 265 | 0.0322 |

Example 6: In Vivo Pharmacodynamic Study of Compound of Formula I on Subcutaneous Xenograft Tumor Model of Human Prostate Cancer LNCaP-FGC Cells 1. Experimental Design

TABLE 4

Preparation method for test substance

| Compound | Preparation method | Concentration (mg/mL) | Storage conditions |
|---|---|---|---|
| Vehicle | 5% DMSO + 40% PEG400 + 10% Solutol + 45% H₂O | — | 4° C. |
| Compound of formula I of Example 1 10 mg/kg | 12.6 mg of the compound of formula I was weighed and dissolved in 0.63 mL of DMSO by vortexing, and the resulting solution was added with 5.04 mL of PEG400, 1.26 mL of Solutol and 5.67 mL of H₂O, and vortexed to give a homogeneous solution | 1 | 4° C. |
| Compound of formula I of Example 1 20 mg/kg | 25.2 mg of the compound of formula I was weighed and dissolved in 0.63 mL of DMSO by vortexing, and the resulting solution was added with 5.04 mL of PEG400, 1.26 mL of Solutol and 5.67 mL of H₂O, and vortexed to give a homogeneous solution | 2 | 4° C. |

Note:
the drugs are required to be gently mixed well before administration to the animlas.

Note: the drugs are required to be gently mixed well before administration to the animals.

TABLE 5

Animal grouping and administration regimen in in vivo pharmacodynamic experiment

| Group | Number of animals | Compound treatment | Dosage (mg/kg) | Administration volume parameter (μL/g) | Route of administration | Frequency of administration |
|---|---|---|---|---|---|---|
| 1 | 6 | Vehicle | — | 10 | PO | QD × 21 days |
| 2 | 6 | Compound of formula I of Example 1 | 10 | 10 | PO | QD × 21 days |
| 3 | 6 | Compound of formula I of Example 1 | 20 | 10 | PO | QD × 21 days |

2. Experimental Materials
2.1 Experimental Animals
Species: mouse
Strain: CB-17 SCID mouse
Week age and body weight: 6-8 weeks old, 18-22 g of body weight
Sex: male
Supplier: Beijing Vital River Laboratory Animal Technology Co., Ltd.
Animal certification number: 11400700184227
3. Experimental Methods and Procedures
3.1 Cell Culture
Human prostate cancer LNCaP-FGC cells (ATCC, Manassas, VA) were cultured in vitro, in a monolayer way, in an RPMI1640 medium containing 10% fetal bovine serum at 37° C. and 5% CO2. Routine digestion treatment with pancreatin-EDTA was performed twice a week for passage. When the saturation degree of the cells is 80-90%, the cells were collected, counted and inoculated.
3.2 Tumor Cell Inoculation
0.2 mL ($10 \times 10^6$) of LNCaP-FGC cells ($10 \times 10^6$+Matrigel, 1:1) were inoculated subcutaneously into the right back of each CB-17 SCID mouse. The mice were divided into groups for administration when the mean tumor volume reached 100-150 mm$^3$.
3.3 Tumor Measurement
Tumor diameters were measured twice weekly using a vernier caliper. The calculation formula for tumor volume was: V=0.5a×b$^2$, with a and b representing the long and short diameters of the tumor, respectively. The anti-tumor therapeutic effect of the compound was evaluated by TGI (%) or relative tumor proliferation rate T/C (%). TGI (%)= [(1−(average tumor volume of a treatment group at the end of administration−average tumor volume of the treatment group at the start of administration))/(average tumor volume of a vehicle control group at the end of treatment-average tumor volume of the vehicle control group at the start of treatment)]×100%. The calculation formula for relative tumor proliferation rate T/C (%) was as follows: T/C %=$T_{RTV}/C_{RTV}$×100% ($T_{RTV}$: RTV of treatment group; $C_{RTV}$: RTV of negative control group). Relative tumor volume (RTV) was calculated based on the results of tumor measurement. The calculation formula was: RTV=$V_t/V_0$, wherein $V_0$ was the average tumor volume measured at the time of grouping and administration (i.e., $d_0$), $V_t$ was the average tumor volume at a certain measurement, and the data of $T_{RTV}$ and $C_{RTV}$ were obtained on the same day.
3.4 Statistical Analysis
Statistical analysis included mean and standard error of mean (SEM) of tumor volume at each time point for each group. The treatment group showed the best treatment effect on day 21 after the administration at the end of the experiment, and therefore statistical analysis was performed based on the data to evaluate the differences between groups. Comparison between two groups was analyzed using T-test, comparison among three or more groups was analyzed using one-way ANOVA. If F values were significantly different, Games-Howell method was used for testing. If there was no significant difference in F values, Dunnet (2-sided) method was used for analysis. All data analysis was performed with SPSS 17.0. "P<0.05" was defined as a significant difference.
4. Experimental Results
After 21 days of administration, the compound of formula I showed significant tumor inhibition effect at both 10 mg/kg and 20 mg/kg dosages compared to the solvent control group (T/C=43.93% and 32.37%, respectively; TGI=62.75% and 76.16%, respectively; p=0.003 and p<0.001, respectively). Meanwhile, the animals had good tolerance to the test compound described above.

Example 7: Study on Hygroscopicity of Crystal of Compound of Formula I

Instrument model: SMS DVS Advantage
Test conditions: a sample (10-15 mg) of the crystal of the compound of formula I prepared in Example 2 was placed in a DVS sample tray for testing.
The detailed DVS parameters were as follows:
Balancing: dm/dt=0.01%/min (shortest: 10 min, longest: 180 min)
Drying: drying at 0% RH for 120 min
Temperature: 25° C.
RH (%) test gradient: 10%
Range of RH (%) test gradient: 0%-90%-0%

Experimental Results

Figure 4:
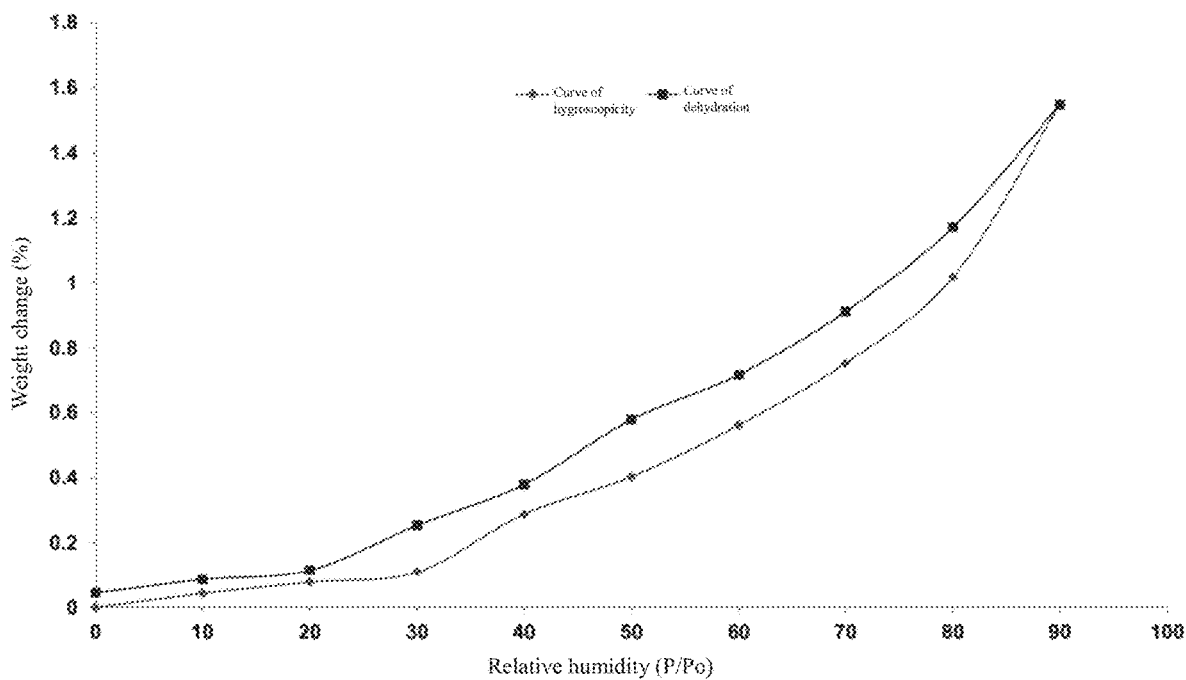
FIG. 4 is a DVS pattern of a crystal of a compound of formula I prepared in Example 2.

The resulting dynamic vapor sorption (DVS) pattern is shown in FIG. 4, wherein ΔW %=1.018%.
Note: ΔW % represents the moisture gain of the test compound at 25±1° C. and 80±2% RH.

Example 8: Experiment on Solid Stability of Crystal of Compound of Formula I

References were made to the requirements in the "Guidelines for the Stability Test of APIs and Preparations" (Appendix XIX C of the Volume Two of the Chinese Pharmacopoeia, 2010 Edition) for the conditions and the method for the stability test of the crystal, and the stability of the crystalline solid under conditions of different influence factors was studied with the crystal prepared in Example 2 as a test sample.
High performance liquid chromatography (HPLC): column: Waters xbridge shiled RP18 (150 mm*4.6 mm, 3.5 μm); PN: 186003045; wavelength: 228 nm; mobile phase A:

pH 4.5, 5 mmol/L sodium acetate buffer solution (pH adjusted with phosphoric acid); mobile phase B: acetonitrile; elution mode: gradient elution. The experimental results are shown in Table 6.

TABLE 6

Stability Analysis of Crystal of Compound of Formula I

| Conditions for stability study | Purity of the crystal of the compound of formula I |
|---|---|
| Initial test sample | 99.17% |
| 92.5% RH, room temperature, 10 days | 99.18% |
| 92.5% RH, room temperature, 10 days | 99.14% |
| 75% RH, 40° C., 10 days | 99.15% |
| 75% RH, 40° C., 1 month | 99.17% |
| 75% RH, 40° C., 2 months | 99.14% |
| 75% RH, 40° C., 3 months | 99.16% |
| 75% RH, 60° C., 10 days | 99.16% |
| 75% RH, 60° C., 1 day | 99.14% |
| The sample was wrapped with tin foil paper and completely exposed to visible light of 1200000 Lux and UV of 200 W at room temperature | 99.13% |

The invention claimed is:

1. A crystal of a compound of formula I,

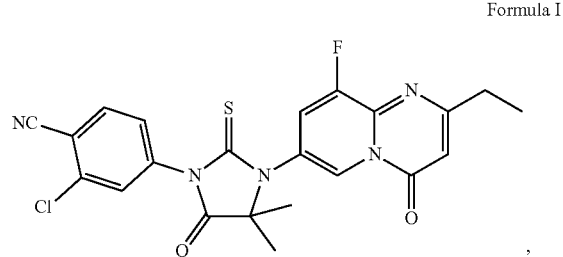 [SMILES: CCc1cc(=O)n2cc(N3C(=S)N(c4ccc(C#N)c(Cl)c4)C(=O)C3(C)C)cc(F)c2n1]

Formula I wherein, in an X-ray powder diffraction pattern using Cu Kα radiation, diffraction peaks exist at 2θ of 13.47°±0.2°, 15.32°±0.2°, 15.98°±0.2°, 18.68°±0.2°, 23.11°±0.2° and 26.41°±0.2°.

2. The crystal of the compound of formula I according to claim 1, wherein the crystal having an absorption peak at 238.92° C. according to differential scanning calorimetry analysis thereof

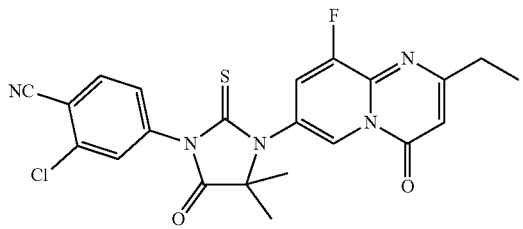

Formula I

3. A crystalline composition, comprising no less than 50 wt % of the crystal of the compound of formula I according to claim 1.

4. A pharmaceutical composition, comprising a therapeutically effective amount of the crystal of the compound of formula I according to claim 1.

5. The crystal of the compound of formula I according to claim 1, wherein, in an X-ray powder diffraction pattern using Cu Kα radiation, diffraction peaks exist at 2θ of 13.01°±0.2°, 13.47°±0.2°, 14.00°±0.2°, 15.32°±0.2°, 15.98°±0.2°, 18.68°±0.2°, 22.78°±0.2°, 23.11°±0.2°, 24.49°±0.2° and 26.41°±0.2°.

6. The crystalline composition according to claim 3, comprising no less than 80 wt % of the crystal of the compound of formula I according to claim 1.

7. The crystalline composition according to claim 6, comprising no less than 90 wt % of the crystal of the compound of formula I according to claim 1.

8. The crystalline composition according to claim 7, comprising no less than 95 wt % of the crystal of the compound of formula I according to claim 1.

9. The pharmaceutical composition according to claim 4, comprising a pharmaceutically acceptable excipient.

* * * * *